US012718447B2

(12) United States Patent
Sommer et al.

(10) Patent No.: US 12,718,447 B2
(45) Date of Patent: Aug. 25, 2026

(54) MOTION CORRECTION USING LOW RESOLUTION MAGNETIC RESONANCE IMAGES

(71) Applicant: KONINKLIJKE PHILIPS N.V., Eindhoven (NL)

(72) Inventors: Karsten Sommer, Hamburg (DE); Christian Wuelker, Hamburg (DE); Christophe Michael Jean Schuelke, Hamburg (DE); Tim Nielsen, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 175 days.

(21) Appl. No.: 18/699,651

(22) PCT Filed: Oct. 4, 2022

(86) PCT No.: PCT/EP2022/077578
§ 371 (c)(1),
(2) Date: Apr. 9, 2024

(87) PCT Pub. No.: WO2023/061808
PCT Pub. Date: Apr. 20, 2023

(65) Prior Publication Data

US 2024/0404131 A1 Dec. 5, 2024

(30) Foreign Application Priority Data

Oct. 11, 2021 (EP) .................................... 21201965

(51) Int. Cl.
*G06T 12/20* (2026.01)
*A61B 5/00* (2006.01)
(Continued)

(52) U.S. Cl.
CPC .............. *G06T 12/20* (2026.01); *A61B 5/055* (2013.01); *A61B 5/7207* (2013.01);
(Continued)

(58) Field of Classification Search
CPC ................ A61B 5/7207; G06T 3/4046; G06T 2207/20084; G06T 2211/441
See application file for complete search history.

(56) References Cited

U.S. PATENT DOCUMENTS

| | | | |
|---|---|---|---|
| 2008/0054899 | A1 | 3/2008 | Aksoy et al. |
| 2013/0278263 | A1 | 10/2013 | Huang et al. |

(Continued)

OTHER PUBLICATIONS

ÂRetrospective Rigid Motion Correction in k-Space for Segmented Radial MRIâ by G. Vaillant et al. IEEE Trans Med Imag. vol. 33, No. 1, Jan. 2014 (Year: 2014).*

(Continued)

*Primary Examiner* — Jason M Ip

(57) ABSTRACT

Described herein is a medical system (100, 300) comprising a memory (110) storing machine executable instructions (120) and an upsampling neural network (122). The upsampling neural network is configured to output an upsampled magnetic resonance image (130) with a second resolution in response to receiving a preliminary magnetic resonance image (126) with a first resolution which is lower than the second resolution. The execution of the machine executable instructions causes a computational system (104) to: receive (200) preliminary k-space data (124); reconstruct (202) the preliminary magnetic resonance image from the preliminary k-space data; receive (204) clinical k-space data (204); receive (206) the upsampled magnetic resonance image in response to inputting the preliminary magnetic resonance image into the upsampling neural network; and provide (208) a motion corrected magnetic resonance image (132) using the upsampled magnetic resonance image and the clinical k-space data.

15 Claims, 6 Drawing Sheets

(51) Int. Cl.

| | |
|---|---|
| ***A61B 5/055*** | (2006.01) |
| ***G06T 3/4046*** | (2024.01) |
| ***G06T 5/50*** | (2006.01) |
| ***G06T 5/60*** | (2024.01) |
| ***G06T 7/00*** | (2017.01) |
| ***G06T 7/11*** | (2017.01) |
| ***G06T 7/246*** | (2017.01) |
| ***G06T 12/30*** | (2026.01) |

(52) U.S. Cl.

CPC .......... *A61B 5/7264* (2013.01); *G06T 3/4046* (2013.01); *G06T 5/50* (2013.01); *G06T 5/60* (2024.01); *G06T 7/0012* (2013.01); *G06T 7/11* (2017.01); *G06T 7/246* (2017.01); *G06T 12/30* (2026.01); *A61B 2576/00* (2013.01); *G06T 2207/10088* (2013.01); *G06T 2207/20016* (2013.01); *G06T 2207/20081* (2013.01); *G06T 2207/20084* (2013.01); *G06T 2207/20224* (2013.01); *G06T 2207/30016* (2013.01); *G06T 2207/30104* (2013.01); *G06T 2210/41* (2013.01); *G06T 2211/441* (2023.08)

(56) References Cited

U.S. PATENT DOCUMENTS

| | | | |
|---|---|---|---|
| 2018/0356484 | A1 | 12/2018 | Boernert et al. |
| 2020/0284866 | A1* | 9/2020 | Kim ..................... G06N 3/0464 |
| 2020/0341100 | A1 | 10/2020 | Heukensfeldt Jansen et al. |

OTHER PUBLICATIONS

Mcdonagh Steven et al: “Context-Sensitive Super-Resolution for Fast Fetal Magnetic Resonance Imaging”, Sep. 9, 2017 (Sep. 9, 2017) Advances in Biometrics : International Conference, Aug. 27-29, 2007 p. 116-126.

Hao Li et al: “Edge, Structure and Texture Refinement for Retrospective High Quality MRI Restoration using Deep Learning”, arxiv.org, Cornell University Library, 201 Olin Library Cornell University Ithaca, NY 14853, Jan. 30, 2021 (Jan. 30, 2021) p. 3-12.

Lucilio Cordero-Grande et al.,“Sensitivity Encoding for Aligned Multishot Magnetic Resonance Reconstruction” IEEE Transactions on Computational Imaging vol. 2., No. 3 Sep. 2016.

International Search Report and Written Opinion from PCT/EP2022/077578 dated Jan. 26, 2023.

Nielsen, T., Boernert B., 2016. Auto-calibrated Iterative SENSE Reconstruction with Rejection of Inconsistent Data, Proc ISMRM 2016, #1863.

Shi, W., et al., 2016. Real-time single image and video super-resolution using an efficient sub-pixel convolutional neural network. In Proceedings of the IEEE conference on computer vision and pattern recognition, pp. 1874-1883.

Huang X, Belongie S. Arbitrary Style Transfer in Real-time with Adaptive Instance Normalization, arXiv:1703.06868v2, 2017.

Ma, D., et al., 2013. Magnetic resonance fingerprinting. Nature, 495(7440), pp. 187-192.

Veronica Corona et al: “Variational Multi-Task MRI Reconstruction: Joint Reconstruction, Registration and Super-Resolution”, arxiv.org, Aug. 16, 2019(Aug. 16, 2019), XP081464350.

* cited by examiner

MOTION CORRECTION USING LOW RESOLUTION MAGNETIC RESONANCE IMAGES

CROSS REFERENCE TO RELATED APPLICATIONS

This application is a U.S. national phase application of International Application No. PCT/EP2022/077578 filed Oct. 4, 2022, which claims the benefit of EP Application Serial No. 21201965.7 filed on Oct. 11, 2021 and is incorporated herein by reference.

TECHNICAL FIELD

The invention relates to magnetic resonance imaging, in particular to motion correction during magnetic resonance imaging.

BACKGROUND

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. Spatial encoding in magnetic resonance imaging is performed using a combination of a radio frequency (RF) waveform (or RF pulse) that is used to control the transmit coil of the MRI scanner and multiple spatially selective gradient pulse waveforms (gradient pulses). A difficulty in performing magnetic resonance imaging is that it can take considerable time to acquire enough data to reconstruct an image. MRI techniques in general are susceptible to subject motion.

Unites States patent application publication US 20130278263 A1 discloses Magnetic Resonance (MR) calibration data that is acquired using a plurality of radio frequency receive coils, and both coil sensitivity maps and reference projection vectors are generated based on the MR calibration data. During imaging, extra navigator projection vectors are acquired, or part of the imaging data can be used as navigator projection vectors. Partially parallel imaging (PPI) can be performed to enhance the navigation information. The navigator projection vectors and the reference projection vectors are sensitivity weighted using the coil sensitivity maps to generate navigator sensitivity weighted projection vectors (navigator SWPV) and reference sensitivity weighted projection vectors (reference SWPV) respectively, and these are compared to generate subject position information. The subject motions are compensated prospectively or retrospectively using the generated subject position information. The motion compensation may be prospective, performed by adjusting an imaging volume of the PPI based on the subject position information.

SUMMARY

The invention provides for a medical system, a computer program, and a method in the independent claims. Embodiments are given in the dependent claims.

Embodiments may provide for a means of compensating for motion of the subject by using a lower resolution preliminary magnetic resonance image (such as a scout image) to enable the providing of a motion corrected magnetic resonance image. This is accomplished by using an upsampling neural network (super-resolution neural network) to convert the preliminary magnetic resonance image to an upsampled magnetic resonance image. The upsampled magnetic resonance image may then be used in various motion correction schemes to provide a motion corrected magnetic resonance image from clinical k-space data.

In one aspect the invention provides for a medical system that comprises a memory that stores machine-executable instructions and also stores an upsampling neural network. The upsampling neural network is configured to output an upsampled magnetic resonance image with a second resolution in response to receiving a preliminary magnetic resonance image with a first resolution. The second resolution is higher than the first resolution. The upsampling neural network therefore provides an upsampled magnetic resonance image with a higher resolution than the preliminary magnetic resonance image that was input to it.

The upsampling neural network may be a neural network that is configured for image processing. The upsampling neural network may in some instances be known as an upsampler or super-resolution neural network. Methods for training the upsampling neural network are known. In some cases, a generative adversarial network may be used. Upsampling by neural networks may be formed with a convolutional neural network that is configured for image processing. The upsampling neural network can be trained by taking images of the second resolution and then creating a training set of data by converting these images of the second resolution to the first resolution. The paired groups of first and second resolution images can then be used for example for deep learning. A sub-pixel conversion neural network was used for the proof of concept (POC) study described below. The sub pixel conversion neural network would be suitable for implementing the upsampling neural network.

The medical system further comprises a computational system. Execution of the machine-executable instructions causes the computational system to receive preliminary k-space data descriptive of a region of interest of a subject at the first resolution. Execution of the machine-executable instructions further causes the computational system to reconstruct the preliminary magnetic resonance image from the preliminary k-space data. Execution of the machine-executable instructions further causes the computational system to receive clinical k-space data descriptive of a region of interest of the subject at the second resolution. Execution of the machine-executable instructions further causes the computational system to receive the upsampled magnetic resonance image in response to inputting the preliminary magnetic resonance image into the upsampling neural network. Finally, execution of the machine-executable instructions further causes the computational system to provide a motion corrected magnetic resonance image using the upsampled magnetic resonance image and the clinical k-space data.

The upsampled magnetic resonance image may be used in a variety of ways to provide the motion corrected magnetic resonance image. For example, the upsampled magnetic resonance image can be converted back into k-space and used to locate regions of corrupt k-space in the clinical k-space data. Once these regions of corrupt k-space have been identified they can for example be used to control the medical system to reacquire the k-space data or perform an operation to correct any corrupted k-space data.

In another embodiment the medical system further comprises a magnetic resonance imaging system. The memory further contains preliminary pulse sequence commands and clinical pulse sequence commands. The preliminary pulse sequence commands are configured to control the magnetic resonance imaging system to acquire the preliminary k-space data. The clinical pulse sequence commands are configured to control the magnetic resonance imaging system to acquire the clinical k-space data. Execution of the machine-executable instructions further causes the computational system to acquire the preliminary k-space data by controlling the magnetic resonance imaging system with the preliminary pulse sequence commands.

Execution of the machine-executable instructions further causes the computational system to acquire the clinical k-space data by controlling the magnetic resonance imaging system with the clinical pulse sequence commands. This embodiment may be beneficial because the medical system has a means of providing for the motion corrected magnetic resonance image. For example, the upsampled magnetic resonance image could be useful for both prospective and retrospective motion correction of the clinical k-space data.

In another embodiment the preliminary k-space data is acquired using a first magnetic resonance imaging modality. A magnetic resonance imaging modality as used herein encompasses the idea of a particular type of protocol used for acquiring a magnetic resonance image. For example, when magnetic resonance images are acquired, there is an option of various weightings such as T1, T2 or other weighting factors which may be encoded. Various repetition times may also be altered which may affect the contrast or other image properties. A magnetic resonance imaging modality is often referred to in the art or colloquially as a contrast. The clinical k-space data is acquired using a second magnetic resonance imaging modality. Providing the motion corrected magnetic resonance image comprises providing a simulated magnetic resonance image using the upsampled magnetic resonance image. The simulated magnetic resonance image has the second resolution and the second magnetic resonance imaging modality. This embodiment may be very beneficial because not only is the resolution increased but the simulated magnetic resonance image may be used to provide an upsampled magnetic resonance image even if the contrast or configuration during the two acquisitions of k-space data are completely different. This for example enables a preliminary scan of a first type to be useful in helping to provide motion correction for the clinical magnetic resonance image even if it is using a different imaging modality or contrast.

In another embodiment the first magnetic resonance imaging modality is identical with the second magnetic resonance imaging modality. In this case there is no need to convert between the various imaging modalities or contrasts.

In another embodiment the simulated magnetic resonance image is provided by the upsampling neural network that is configured to output the upsampled magnetic resonance image as the simulated magnetic resonance image. In this case for example the scaling neural network may perform both the upsampling and the imaging modality or contrast conversion.

In another embodiment the memory further contains a second resolution modality conversion neural network configured to output the simulated magnetic resonance image in response to receiving the upsampled magnetic resonance image. The second resolution modality conversion neural network is a modality conversion neural network configured to convert the modality or "contrast" of magnetic resonance images which have the second resolution. Execution of the machine-executable instructions further causes the computational system to receive the simulated magnetic resonance image in response to inputting the upsampled magnetic resonance image into the second resolution modality conversion neural network. Neural networks such as U-net, F-net, or other image processing neural networks may be suitable for implementing the second resolution modality conversion neural network. The second resolution modality conversion neural network may be trained by acquiring two images from the same subject using the two different modalities. In this example the preliminary magnetic resonance image is first upsampled and then the image conversion to the second modality is performed.

In another embodiment the memory further contains a first resolution modality conversion neural network (which may be similarly implemented and trained) that is configured to convert the preliminary magnetic resonance image from the first magnetic resonance imaging modality to the second magnetic resonance imaging modality. Execution of the machine-executable instructions further causes the computational system to receive a converted preliminary magnetic resonance image in response to inputting the preliminary magnetic resonance image into the first resolution modality conversion neural network. The upsampling neural network is configured to output the upsampled magnetic resonance image as the simulated magnetic resonance image in response to receiving the converted preliminary magnetic resonance image as input. In this example the contrast or modality conversion is performed first and then the image is upsampled.

The first resolution modality conversion neural network and the second resolution modality conversion neural network may have analogous structures and be trained in analogous manners.

In another embodiment the providing of a motion corrected magnetic resonance image using the upsampled magnetic resonance image and the clinical k-space data comprises performing a motion-compensated reconstruction of the motion corrected magnetic resonance image using the upsampled magnetic resonance image or the simulated magnetic resonance image.

In another embodiment the motion-compensated reconstruction is performed as an optimization that uses the upsampled magnetic resonance image or the simulated magnetic resonance image as an intermediate estimate of the motion free image to be reconstructed. This embodiment may be beneficial because using the upsampled magnetic resonance image or the simulated magnetic resonance image as a motion free image provides a means of improving the quality of the optimization, as well as to reduce computation times.

In another embodiment the motion-compensated reconstruction comprises determining a phase of the motion free image to be reconstructed using a phase map determined at least partially from the clinical k-space data. This embodiment may be beneficial because the phase of k-space data derived from the upsampled magnetic resonance image may be incorrect. An improved motion correction can therefore be performed by taking the amplitude from the upsampled image and taking the phase from the original clinical k-space data.

In another embodiment execution of the machine-executable instructions further causes the computational system to calculate simulated k-space data by performing a Fourier transform of the simulated magnetic resonance imaging data or the upsampled magnetic resonance image. For parallel imaging techniques, this may include multiplying the simulated imaging data with the coil sensitivity maps and Fourier transform these images, whose k-spaces can then directly be compared to the k-space data acquired by each of the coil elements.

Execution of the machine-executable instructions further causes the computational system to detect motion corrupted k-space data by comparing the simulated k-space data to the clinical k-space data. Execution of the machine-executable instructions further causes the computational system to limit the optimization to the motion corrupted k-space data. In this embodiment the regions of the clinical k-space data can be estimated with the simulated k-space data. The speed and quality of the optimization may be greatly improved by limiting optimization to only the region which is detected as having the corrupted k-space data.

In another embodiment the providing of the motion corrected magnetic resonance image using the upsampled magnetic resonance image and the clinical k-space data comprises calculating the simulated k-space data by performing a Fourier transform of the simulated magnetic resonance imaging data. As was mentioned above, in parallel imaging this may include multiplying the simulated imaging data with the coil sensitivity maps and Fourier transform these images, whose k-spaces can then directly be compared to the k-space data acquired by each of the coil elements.

This embodiment further comprises detecting motion corrupted k-space data by comparing the simulated k-space data to the clinical k-space data and then finally reacquiring the motion corrupted k-space data and/or adjusting the acquisition of the clinical k-space data to compensate for the subject motion. In this embodiment the simulated k-space data is used to detect motion corrupted k-space data and then cause a reacquisition of this data. This may provide for superior reconstruction of the motion corrected magnetic resonance image when the k-space data is so corrupted that it is not feasible or desirable to reconstruct it.

In another embodiment, providing the motion corrected magnetic resonance image using the upsampled magnetic resonance image and the clinical k-space data comprises calculating simulated k-space data by performing a Fourier transform of the simulated magnetic resonance imaging data; determining motion parameters by comparing the simulated k-space data and the clinical k-space data; and reconstructing the motion corrected magnetic resonance image from the clinical k-space data using a motion-correction algorithm that receives the motion parameters as input. For example, the motion-correction algorithm may shift or translate at least a portion of the clinical k-space data using the motion parameters before reconstruction of the motion corrected magnetic resonance image.

In another embodiment, execution of the machine executable instructions further causes the computational system to reconstruct a preliminary image from the clinical k-space data. Execution of the machine executable instructions further causes the computational system to determine an image registration between the preliminary image and the simulated magnetic resonance imaging data. Execution of the machine executable instructions further causes the computational system to use this image registration when comparing the simulated k-space data and the clinical k-space data in the above-described embodiments. For example, this may be used to compensate or correct for subject motion between the preliminary magnetic resonance imaging acquisition and the clinical magnetic resonance imaging acquition. This may for example be useful in detecting which portions of the clinical k-space data were motion corrupted. This could be done by registering the simulated k-space data and a preliminary image that is a motion-corrupted image, which would most likely register the simulated image with the dominant motion state of the corrupted image. (On the contrary, if the motion segments are considered known and the upsampled image is used to estimate motion parameters, this step is not crucial—the estimated motion parameters will simply be different.)

In another embodiment the second resolution is at least 1.5 times greater than the first resolution.

In another embodiment the second resolution is at least 2 times greater than the first resolution.

In another embodiment the second resolution is at least 3 times greater than the first resolution.

In another embodiment the second resolution is at least 4 times greater than the first resolution.

In another embodiment the preliminary k-space data is at least partially coil calibration k-space data that is acquired from multiple magnetic resonance imaging coil elements. Execution of the machine-executable instructions further causes the computational system to reconstruct a coil image for each of the multiple magnetic resonance imaging coil elements. Execution of the machine-executable instructions further causes the computational system to construct the preliminary magnetic resonance image by combining at least the coil image for each of the multiple magnetic resonance imaging coil elements. This embodiment may be beneficial because it may provide for a means of improving parallel imaging (such as sense imaging) reconstruction of magnetic resonance images.

In another embodiment the preliminary k-space data is at least partially acquired from a body coil. This embodiment may be beneficial because the low-resolution image that is typically acquired with a body coil may be used to provide motion correction for higher resolution clinical images.

In another embodiment the preliminary k-space data is magnetic resonance fingerprinting k-space data. The preliminary magnetic resonance image is a quantitative magnetic resonance image. This embodiment may be particularly beneficial because it may be straightforward to convert the magnetic resonance fingerprinting data into a pseudo magnetic resonance image that can be used for motion correction.

In another aspect the invention provides for a computer program that comprises machine-executable instructions for execution by a computational system and an upsampling neural network which may also be for execution by the computational system. The computer program may be stored on a non-transitory storage medium and may be a computer program product. The upsampling neural network is configured to output an upsampled magnetic resonance image with a second resolution in response to receiving a preliminary magnetic resonance image with a first resolution. The second resolution is higher than the first resolution.

Execution of the machine-executable instructions further causes the computational system to receive preliminary k-space data descriptive of a region of interest of the subject at the first resolution. Execution of the machine-executable instructions further causes the computational system to reconstruct the preliminary magnetic resonance image from the preliminary k-space data. Execution of the machine-executable instructions further causes the computational system to receive clinical k-space data descriptive of the region of interest of the subject at the second resolution. Execution of the machine-executable instructions further causes the computational system to receive the upsampled magnetic resonance image in response to inputting the preliminary magnetic resonance image into the upsampling neural network. Execution of the machine-executable instructions further causes the computational system to provide a motion corrected magnetic resonance image using the upsampled magnetic resonance image and the clinical k-space data.

In another aspect the invention provides for a method of medical imaging. The method comprises receiving preliminary k-space data descriptive of a region of interest of a subject at a first resolution. The method further comprises reconstructing a preliminary magnetic resonance image from the preliminary k-space data. The method further comprises receiving clinical k-space data descriptive of the region of interest of the subject at a second resolution. The second resolution is higher than the first resolution. The method further comprises receiving the upsampled magnetic resonance image in response to inputting the preliminary magnetic resonance image into an upsampling neural network. The upsampling neural network is configured to output an upsampled magnetic resonance image with the second resolution in response to receiving the preliminary magnetic resonance image with the first resolution. The method further comprises providing a motion corrected magnetic resonance image using the upsampled magnetic resonance image and the clinical k-space data.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance Imaging (MRI) image or MR image is defined herein as being the reconstructed two- or three-dimensional visualization of anatomic data contained within the k-space data.

This visualization can be performed using a computer.

BRIEF DESCRIPTION OF THE DRAWINGS

In the following preferred embodiments of the invention will be described, by way of example only, and with reference to the drawings in which.

DESCRIPTION OF EMBODIMENTS

Like numbered elements in these figures are either equivalent elements or perform the same function. Elements which have been discussed previously will not necessarily be discussed in later figures if the function is equivalent.

Figure 1:
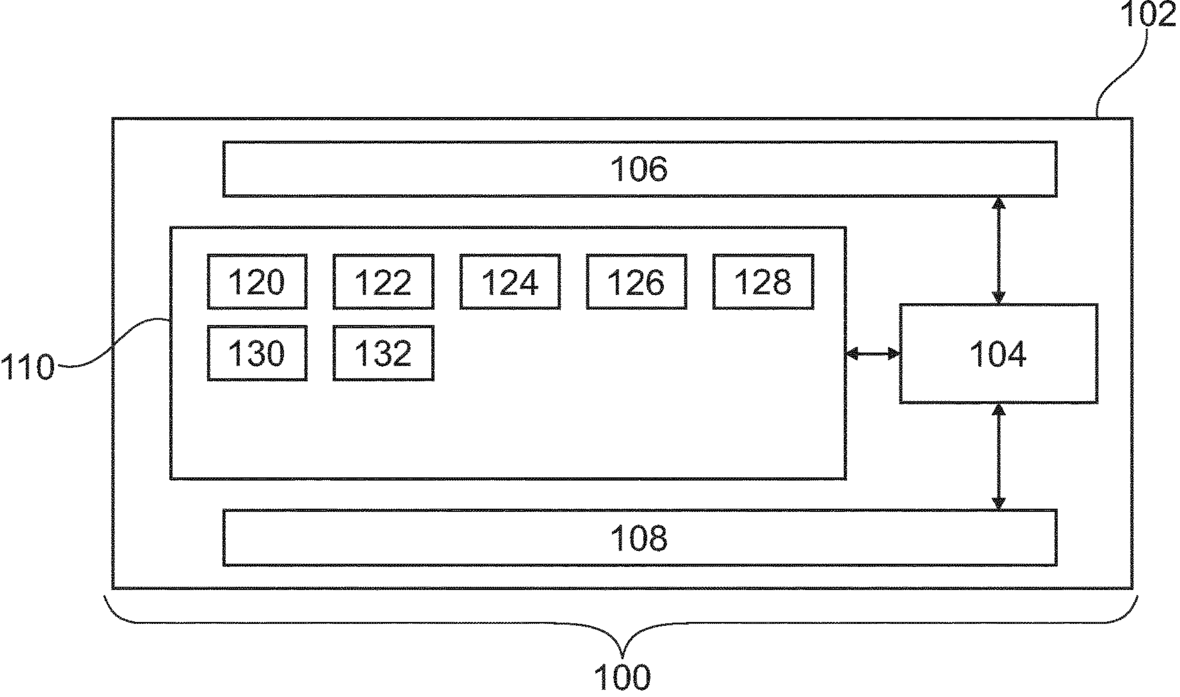
FIG. 1 illustrates an example of a medical instrument.

FIG. 1 illustrates an example of a medical system 100. The medical system 100 is shown as comprising a computer 102. The computer 102 is intended to represent one or more computer systems that may be in the same location or may be distributed. The computer 102 is shown as comprising a computational system that is in communication with an optional hardware interface 106, an optional user interface 108, and a memory 110. The computational system 104 is intended to represent one or more computational systems that may be at one or more locations. The computational system 104 could be integrated into the control system of a magnetic resonance imaging system, located on a computer system for a radiology department, or may even be available as a web-based or cloud-based service. The hardware interface 106 may enable the computational system 104 to communicate and/or control other components of the medical system 100. For example, if a magnetic resonance imaging system is present the hardware interface 106 will enable the computational system 104 to control the magnetic resonance imaging system. The user interface 108 may provide a means for an operator or user to control the operation and function of the medical system 100.

The memory 110 is intended to represent different types of memory which may be available or accessible to the computational system 104. The memory 110 is shown as comprising machine-executable instructions 120. The machine-executable instructions 120 are instructions that enable the computational system 104 to perform various tasks such as image processing, numerical calculations, and the control of other components. The memory 110 is further shown as containing an upsampling neural network 122 that is configured for receiving a preliminary magnetic resonance image 126 and upsampling it to an upsampled magnetic resonance image 130.

The memory 110 is further shown as containing preliminary k-space data 124; it may for example then receive a network interface, retrieved from storage or may be acquired directly by a magnetic resonance imaging system. The memory 110 is further shown as containing a preliminary magnetic resonance image 126 that has been reconstructed from the preliminary k-space data 124. The memory 110 is further shown as containing clinical k-space data 128. The clinical k-space data 128 is descriptive of a region of interest of a subject and has a second resolution. The preliminary k-space data 124 is descriptive of the same region of interest and has a first resolution. The second resolution is higher than the first resolution.

The memory 110 is shown as containing an upsampled magnetic resonance image 130 that was obtained from the upsampling neural network 122 by inputting the preliminary magnetic resonance image 126. The upsampled magnetic resonance image 130 has the second resolution. The memory is further shown as containing a motion corrected magnetic resonance image 132 that was reconstructed using the clinical k-space data 128 and the upsampled magnetic resonance image 130. The upsampled magnetic resonance image 130 may be used in a variety of ways to aid in motion correction when reconstructing the clinical k-space data 128 into the motion corrected magnetic resonance image 132. For example, the upsampled magnetic resonance image 130 may be converted into k-space and this may be used to locate or determine corrupted portions of the clinical k-space data 128. In other instances, the upsampled magnetic resonance image 130 may be used as a reference image for a reconstruction of the motion corrected magnetic resonance image 132.

Figure 2:
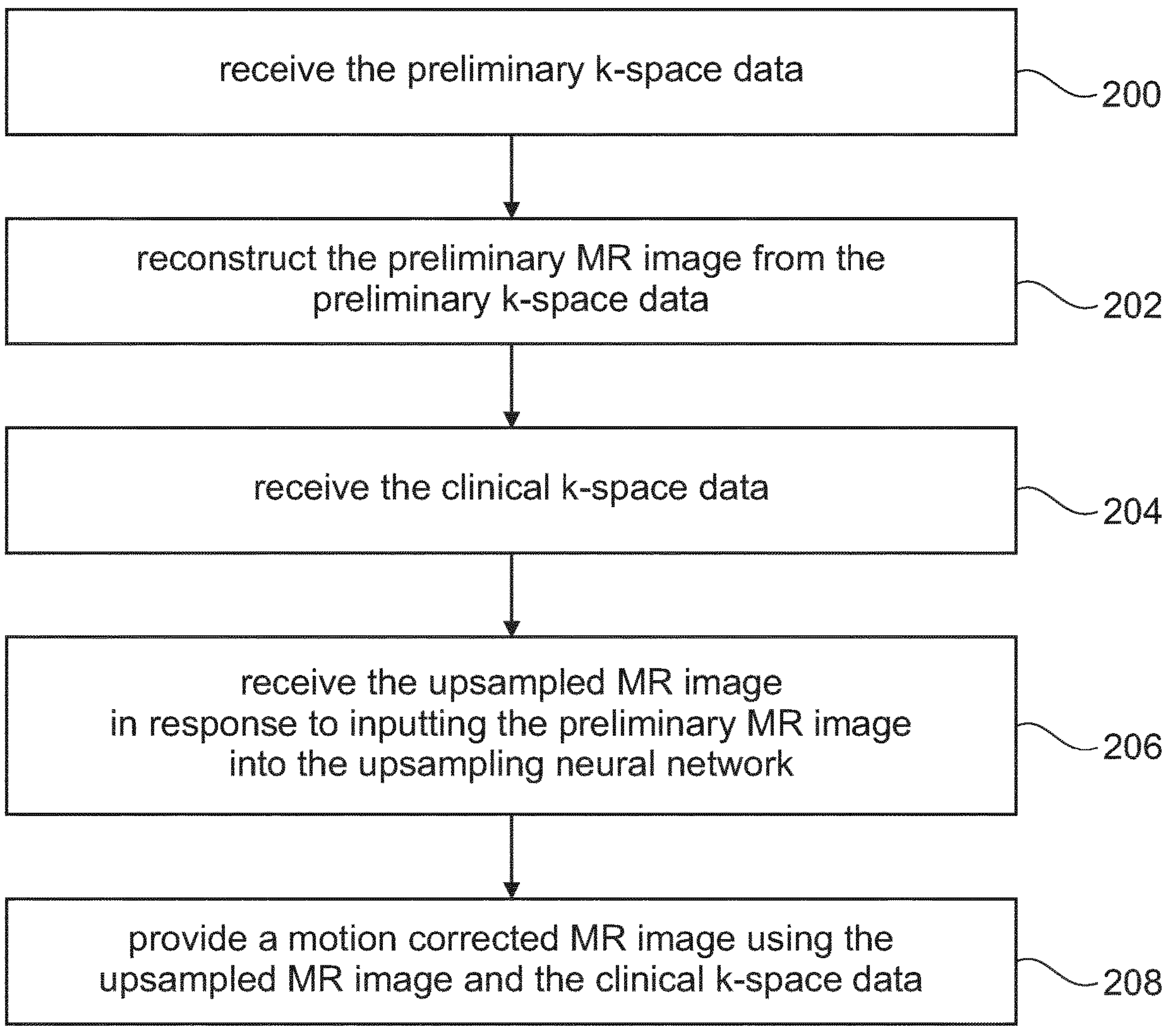
FIG. 2 shows a flow chart which illustrates a method of using the medical instrument of FIG. 1.

FIG. 2 shows a flowchart which illustrates a method of operating the medical system 100 of FIG. 1. First, in step 200, the preliminary k-space data 124 is received. Next, in step 202, the preliminary magnetic resonance image 126 is reconstructed from the preliminary k-space data 124. Then, in step 204, the clinical k-space data 128 is received. Next, in step 206, the upsampled magnetic resonance image 130 is received in response to inputting the preliminary magnetic resonance image into the upsampling neural network 122. Then finally, in step 208, the motion corrected magnetic resonance image 132 is provided using the upsampled magnetic resonance image 130 and the clinical k-space data 128.

Figure 3:
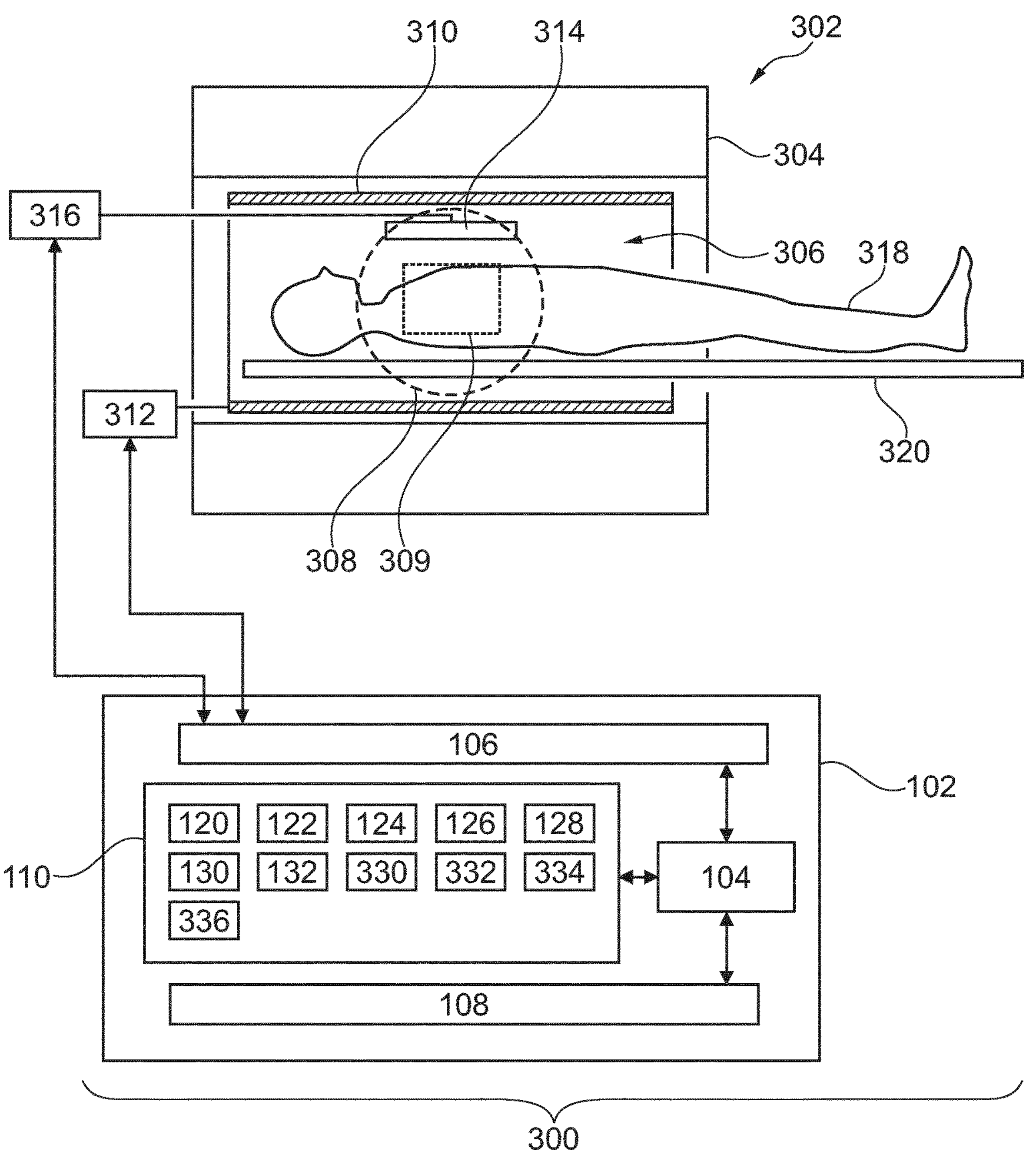
FIG. 3 illustrates a further example of a medical instrument.

FIG. 3 illustrates a further example of a medical system 300. The medical system 300 depicted in FIG. 3 is similar to the medical system 100 depicted in FIG. 1 except it additionally comprises a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A field of view 309 is shown within the imaging zone 308. The magnetic resonance data that is acquired typically acquired for the field of view 309. The region of interest could be identical with the field of view 309 or it could be a sub volume of the field of view 309. A subject 318 is shown as being supported by a subject support 320 such that at least a portion of the subject 318 is within the imaging zone 308 and the field of view 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels.

The transceiver 316 and the gradient controller 312 are shown as being connected to the hardware interface 106 of the computer system 102. Both of these components, as well as others such as the subject support supplying positional data, may supply the sensor data 126.

The memory 110 is shown as containing preliminary pulse sequence commands 330 and clinical pulse sequence commands 332 that are configured for controlling the magnetic resonance imaging system 302 to acquire the preliminary k-space data 124 and the clinical k-space data 128 respectively. The memory is further shown as containing a modality conversion neural network 334 that is used to convert the modality or contrast of a magnetic resonance image. The modality conversion neural network could for example be a first resolution modality conversion neural network or a second resolution modality conversion neural network.

The preliminary k-space data 124 and the clinical k-space data 128 may be acquired using different contrasts. For example, the preliminary k-space data 124 may be a simple proton density image acquired at relatively low resolutions as a scout or pilot image. The clinical k-space data 128 could have a different contrast such as being a T1 or T2 weighted image. The modality conversion neural network 334 is used in conjunction with the upsampling neural network 122. They could for example be configured in different ways. In one instance the upsampling neural network 122 is first used and then the modality conversation neural network 334 is used (in this case the modality conversion neural network 344 is a second resolution modality conversion neural network). In other configurations the modality conversion neural network 334 is first used and then the upsampling neural network 122 (in this case the modality co version neural network is a first resolution modality conversion neural network). In either case, the result of using the two neural networks 334, 122 is to have a simulated magnetic resonance image 336 that has the same modality or contrast as the clinical k-space data 128 and the same second resolution. The simulated magnetic resonance image 336 or the upsampled magnetic resonance image 130 is then used to provide the motion corrected magnetic resonance image with the clinical k-space data. This may for example be performed by doing a motion-compensated reconstruction of the motion corrected magnetic resonance image 132. For example, the motion-compensated reconstruction may perform an optimization that uses the upsampled magnetic resonance image 130 or the simulated magnetic resonance image 336 as a motion free image during this reconstruction.

Figure 4:
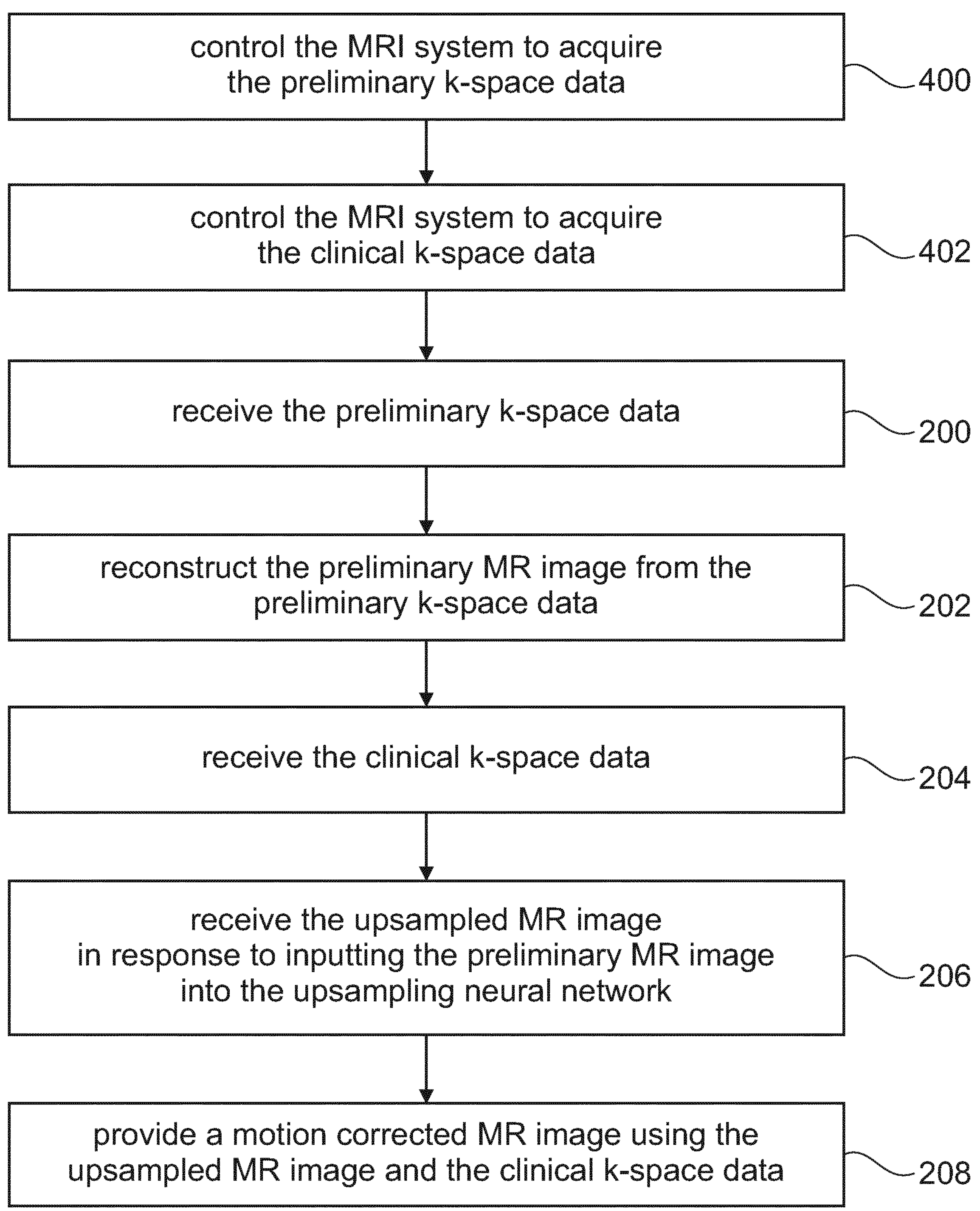
FIG. 4 shows a flow chart which illustrates a method of using the medical instrument of FIG. 3.

FIG. 4 shows a flowchart which illustrates a further method of operating the medical system 300 of FIG. 3. First, in step 400, the preliminary k-space data is acquired by controlling the magnetic resonance imaging system 302 with the preliminary pulse sequence commands 330. Then, in step 402, the clinical k-space data 128 is acquired by controlling the magnetic resonance imaging system 302 with the clinical pulse sequence commands 332. After step 402, steps 200, 202, 204, 206, and 208 are performed as is illustrated in FIG. 1.

Examples may provide for a method that uses at least one dedicated neural network (upsampling neural network 122 and possibly modality conversion neural network 334) to transform a low-resolution pre-scan (preliminary magnetic resonance image 126) to obtain a high-resolution estimate of the following anatomical scans (T1w, T2w, etc.). In a first step, a super-resolution network (upsampling neural network 122) upsamples the pre-scan data to the target resolution (second resolution). In a second step, a dedicated network converts the data to the target contrast.

In case of patient motion during one of the anatomical scans, this converted pre-scan may be used in one example as a motion-free reference to identify corrupted parts of k-space and to estimate the relevant motion parameters. This information is employed in the following in a motion-compensated reconstruction. Alternatively, identification of corrupted k-space profiles can be performed in real time during data acquisition of the anatomical scan, thereby guiding appropriate data re-acquisition to reduce motion artifacts.

Degradation of image quality due to patient motion is one of the most frequent problems in the clinical application of MRI. Many patients have difficulties remaining calm throughout the entire scan. Retrospective correction of motion artifacts relies on the accurate identification of corrupted parts of k-space and/or estimation of a set of parameters that describe the patient motion. Previously proposed methods for this task either lack robustness or involve extremely long reconstruction times. Improved methods for corrupted shot identification and motion parameter estimation have the potential to substantially reduce these computation times.

Examples may use pre-scan data such as the Sense reference scan (SenseRefScan) to obtain an estimate of the following anatomical scans. This is achieved using in some examples two dedicated networks for super-resolution (upsampling neural network) and contrast conversion (modality conversion neural network). The resulting converted pre-scan data is then employed to identify corrupted parts of k-space and/or to estimate relevant motion parameters as part of a motion-compensated reconstruction.

Figure 5:
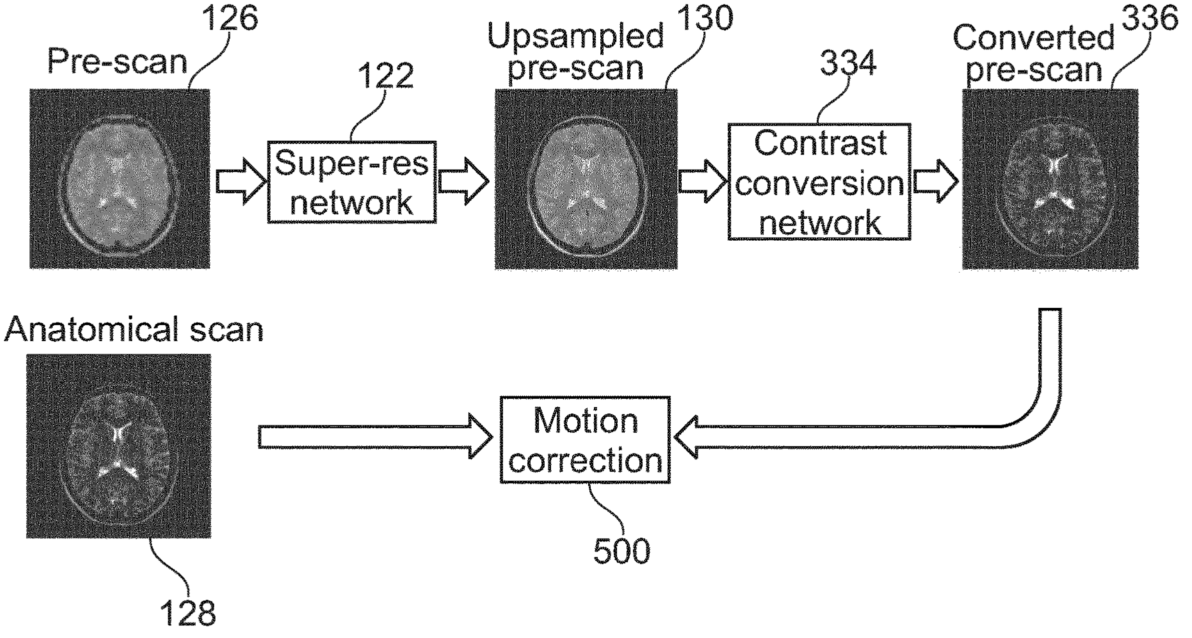
FIG. 5 illustrates a further example of a method.

An overview of an example method is shown in FIG. 5. FIG. 5 shows a flowchart which graphically represents a method of imaging. In this example, the preliminary magnetic resonance image 126 or pre-scan is fed into an upsampling neural network 122, which may also be referred to as a super-res network. This results in an upsampled magnetic resonance image 130 which may also be referred to as an upsampled pre-scan. The pre-upsampled magnetic resonance image 130 is then fed into the modality conversion neural network 334 or a contrast conversion network. This results in a simulated magnetic resonance image 336, which may also be referred to as a converted pre-scan image. The example in FIG. 5 only represents one possibility. If the images are of the same modality then the modality conversion neural network 334 can be skipped as it is not necessary to make the simulated magnetic resonance image 336. In a further example, the contrast conversion network 334 is applied before the super-res network 122. In this case the converted image 336 is then upsampled into the upsampled pre-scan 130. In either case, the converted pre-scan 336 is fed into a motion correction algorithm along with the clinical k-space data 128 to calculate the motion corrected magnetic resonance image.

In a first step (122), the pre-scan data (preliminary magnetic resonance image 126) is translated to the target resolution (second resolution) using a super-resolution network (upsampling neural network 122). Various network architectures and training setups can be envisioned for this task. In a proof-of-concept (POC) study, a sub-pixel convolutional neural network was trained on a dataset of high-resolution natural images that were downsampled by a factor of 4.

In a second step, the upsampled pre-scan data (upsampled magnetic resonance image 130) is converted to the target MR contrast using a dedicated contrast conversion network (modality conversion neural network 334). Various imageto-image architectures for this network can be used, such as U Net, F-Net, etc. Creation of a suitable dataset can be realized in multiple ways:

Identify artifact-free scan pairs with identical geometry in a clinical database, create a database using registration of the two scans if necessary.

Acquire quantitative datasets that contain tissue parameter maps to enable forward simulation of arbitrary MR contrasts, i.e. proton density, T1 and T2 maps. Additional tissue parameters such as diffusion, perfusion, etc. may be helpful to extend the method to functional MR sequences.

If matching scan pairs with identical geometry are not available, large datasets of (unpaired) scans may also be used. In this case, a cycleGAN network architecture can be used. To avoid training of a dedicated contrast conversion network for each modification of the scan parameter settings (say, changes of TE and TR), the conversion network can be designed to incorporate these scan settings as additional inputs. One possibility for such a design is the inclusion of adaptive instance normalization (AdaIn) layers in the network.

The converted pre-scan data (denoted by $x_p$, in the following) is then used as prior information in the motion correction module. Multiple implementations of the data processing in this module are possible:

Identification of corrupted parts of k-space can be achieved by subtracting the Fourier transformed converted pre-scan and the acquired anatomical data. Large deviations between these datasets are assumed to correspond to k-space portions that are corrupted by motion and can e.g. be identified by thresholding.

This resulting information can be used as prior information in a motion-compensated reconstruction (see below) to simplify and accelerate the computations, to guide iterative reconstruction approaches that involve a rejection of motion-corrupted data, in real-time motion artifact reduction techniques that aim to re-acquire corrupted parts of k space. Here it can be exploited that all processing steps of the pre-scan dataset can be performed before the anatomical scan is started, thereby allowing for very fast processing of the incoming anatomical data.

Retrospective correction of motion artifacts can be performed using a motion-compensated reconstruction, which may be described by $$\underset{\theta}{\operatorname{argmin}}\|M\mathcal{F}CT_\theta x - y\|$$

where y denotes the measured k-space data, x the motion-free image to be reconstructed, $T_\theta$ a motion transformation matrix parametrized by θ, C the coil sensitivities, $\mathcal{F}$ the Fourier transform and M the appropriate sampling matrix. Since the motion-free image x is not known, the above problem is solved for the motion parameters θ by using the converted pre-scan data $x_p$ instead of x.

A complication of this method is the accurate prediction of the phase of the anatomical scan: since detection of corrupted profiles is performed in k-space, complex data is needed. Several approaches are possible to tackle this problem:

For minor motion artifacts, the phase of the acquired motion-corrupted data can simply be applied to the converted pre-scan magnitude data. Corrupted profiles can still be detected.

Motion artifacts in the phase of the acquired motion-corrupted data are corrected before combining it with the pre-scan magnitude data. For minor artifacts, a simple polynomial fit of the phase can suffice. For more severe artifacts, a dedicated image-to-image network has been found to yield very accurate artifact-free phase images.

The phase map φ of $x_p$ can be estimated simultaneously with the motion parameters θ by solving the combined minimization problem:

$$\underset{\theta,\varphi}{\operatorname{argmin}}\|M\mathcal{F}CT_\theta e^{i\varphi}|x_p| - y\|,$$

which can be solved iteratively if the parameter θ has only few components, for example in the case of rigid motion. φ can be initialized with the motion-corrupted image's phase.

To demonstrate feasibility of the invention, a POC experiment was conducted using 2D high-resolution brain data obtained in a volunteer. The results are shown in FIG. 6.

Figure 6:
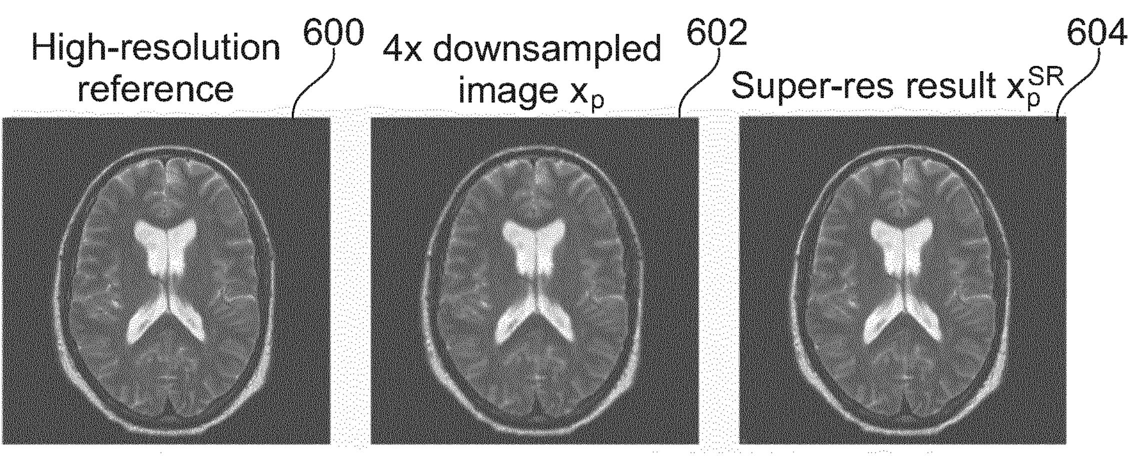
FIG. 6 illustrates results from a proof of concept study.
Figure 6:
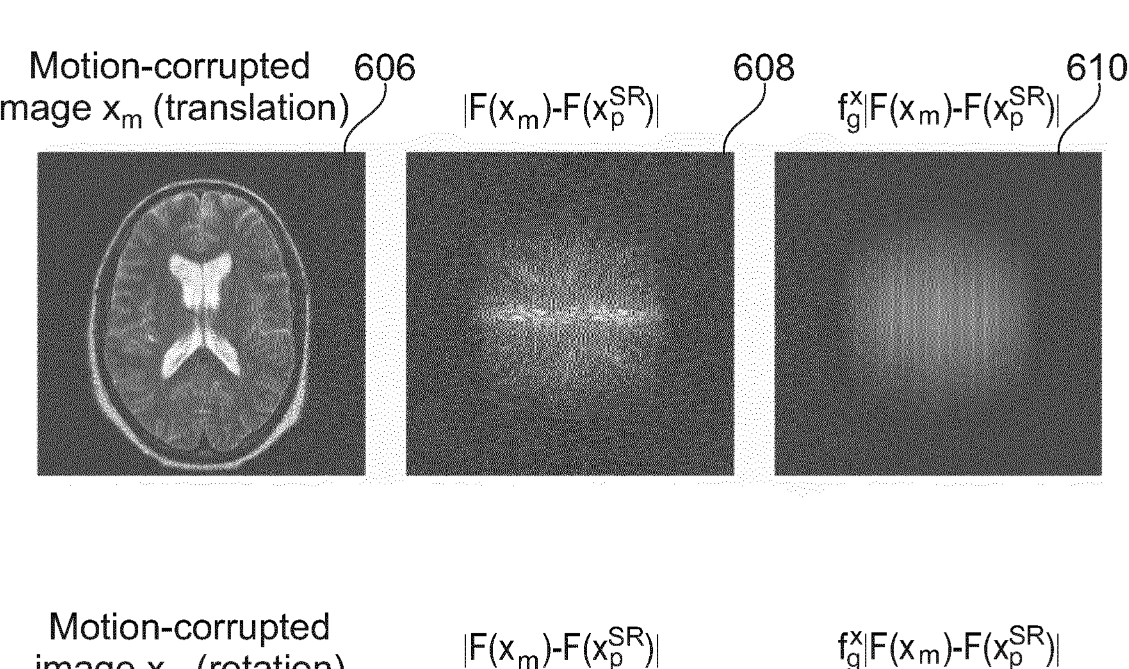
Figure 6:
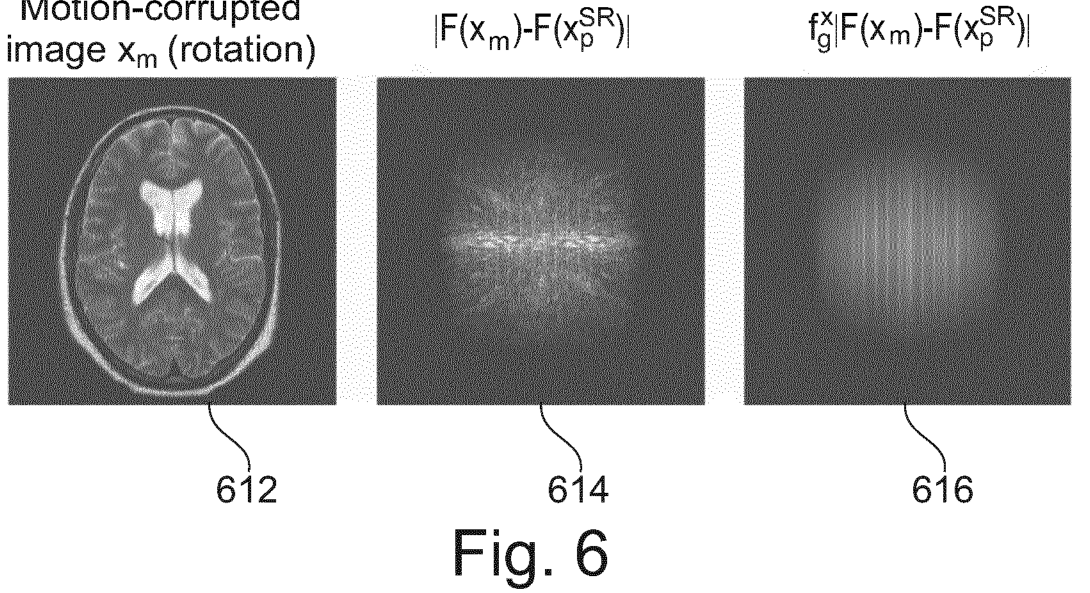

FIG. 6 shows images used in the simulation to demonstrate the effectiveness of the motion correction. Image 600 shows a high-resolution two-dimensional brain scan. Image 602 is the same image as 600 that has been down-sampled by a factor of 4. Image 604 is an image with the same resolution of image 600 but has been constructed by upsampling the image 602 with a super-res neural network. Image 606 shows a motion corrupted image with a translation-induced error for a single shot. Image 608 shows the difference between the motion-corrupted data and the output of the super-res neural network in k-space, where the bright vertical lines correspond to the motion-corrupted shot. Image 610 shows the result of applying a gaussian filter in the vertical direction to the difference image 608. Image 612 shows a motion corrupted image with a rotation-induced error for a single shot. Image 614 shows the difference between the motion-corrupted data and the output of the super-res neural network in k-space, where the bright vertical lines correspond to the motion-corrupted shot. Image 616 shows the result of applying a gaussian filter in the vertical direction to the difference image 614.

The high-resolution input data 600 was first downsampled by a factor of 4 (image 602). This low-resolution "pre-scan" image $x_p$ was then upsampled with a dedicated super-resolution network trained on natural images to obtain an estimate of the input data $$(x_p^{SR}, 604).$$

To test the sensitivity of the approach for motion detection, a TSE readout with echo train length of 28 was assumed, and a single shot was corrupted by a 2px translation (corresponding to 1.4 mm) 608. Subtraction of the upsampled pre-scan and the motion-corrupted data in Fourier domain clearly shows vertical lines corresponding to the corrupted profiles 610. To improve visibility of these corrupted profiles, a gaussian filter was applied in readout direction 612. The corresponding results are shown for a 2° rotation in the bottom row (images 612 to 616).

For the design and application of the described system and method, additional features can be considered:

Instead of using the SENSE reference scan, a dedicated fast pre-scan may be used that yields a lower resolution but the same contrast as the anatomical scan. This way, the contrast conversion step may be skipped, potentially reducing associated errors, i.e. increasing sensitivity of the methods with respect to very weak motion.

A single low-resolution magnetic resonance fingerprinting (MRF) pre-scan can be performed at the beginning of the exam. The resulting quantitative tissue parameter maps (proton density, T1, T2, . . . ) can then be used to give a low-resolution estimate of all following anatomical scans. Again, the contrast conversion step in FIG. 5 can be skipped in this scenario.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST

100 medical system
102 computer
104 computational system
106 optional hardware interface
108 optional user interface
110 memory
120 machine executable instructions
122 upsampling neural network
124 preliminary k-space data
126 preliminary magnetic resonance image
128 clinical k-space data
130 upsampled magnetic resonance image
132 motion corrected magnetic resonance image
200 receive preliminary k-space data descriptive of a region of interest of a subject at the first resolution
202 reconstruct the preliminary magnetic resonance image from the preliminary k-space data
204 receive clinical k-space data descriptive of the region of interest of the subject at the second resolution
206 receive the upsampled magnetic resonance image in response to inputting the preliminary magnetic resonance image into the upsampling neural network
208 provide a motion corrected magnetic resonance image using the upsampled magnetic resonance image and the clinical k-space data
300 medical system
302 magnetic resonance imaging system
304 magnet
306 bore of magnet
308 imaging zone
309 field of view
310 magnetic field gradient coils
312 magnetic field gradient coil power supply
314 radio-frequency coil
316 transceiver
318 subject
320 subject support
330 preliminary pulse sequence commands
332 clinical pulse sequence commands
334 modality conversion neural network
336 simulated magnetic resonance image
400 acquire the preliminary k-space data by controlling the magnetic resonance imaging system with the preliminary pulse sequence commands
402 acquire the clinical k-space data by controlling the magnetic resonance imaging system with the clinical pulse sequence commands
500 image reconstruction algorithm
600 high-resolution reference image
602 downsampled image
604 upsampled image
606 simulated motion corrupted image (translational)
608 motion artifacts in k-space
610 motion artifacts in image space
612 motion corrupted image (rotational)
614 motion artifacts in k-space
616 motion artifacts in image space

The invention claimed is:

1. A medical system comprising:

a memory configured to store machine executable instructions and an upsampling neural network, wherein the upsampling neural network is configured to output an upsampled magnetic resonance image with a second resolution in response to receiving a preliminary magnetic resonance image with a first resolution, wherein the second resolution is higher than the first resolution, a computational system, wherein execution of the machine executable instructions causes the computational system to:

receive preliminary k-space data descriptive of a region of interest of a subject at the first resolution;

reconstruct the preliminary magnetic resonance image from the preliminary k-space data;

receive clinical k-space data descriptive of the region of interest of the subject at the second resolution;

input the preliminary magnetic resonance image into the upsampling neural network and generate and receive from the upsampling neural network the upsampled magnetic resonance image; and generate a motion corrected magnetic resonance image using the upsampled magnetic resonance image and the clinical k-space data.

2. The medical system of claim 1, wherein the medical system further comprises a magnetic resonance imaging system, wherein the memory further contains preliminary pulse sequence commands and clinical pulse sequence commands, wherein the preliminary pulse sequence commands are configured to control the magnetic resonance imaging system to acquire the preliminary k-space data, wherein the clinical pulse sequence commands are configured to control the magnetic resonance imaging system to acquire the clinical k-space data, wherein execution of the machine executable instructions further causes the computational system to:

acquire the preliminary k-space data by controlling the magnetic resonance imaging system with the preliminary pulse sequence commands; and acquire the clinical k-space data by controlling the magnetic resonance imaging system with the clinical pulse sequence commands.

3. The medical system of claim 2, wherein the preliminary k-space data is acquired using a first magnetic resonance imaging modality, wherein the clinical k-space data is acquired using a second magnetic resonance imaging modality, wherein generating the motion corrected magnetic resonance image comprises providing a simulated magnetic resonance image using the upsampled magnetic resonance image, wherein the simulated magnetic resonance image has the second resolution and the second magnetic resonance imaging modality.

4. The medical system of claim 3, wherein the simulated magnetic resonance image is provided by any one of the following:

the first magnetic resonance imaging modality is identical with the second magnetic resonance imaging modality;

the upsampling neural network is configured to output the upsampled magnetic resonance image as the simulated magnetic resonance image;

the memory further contains a second resolution modality conversion neural network configured to output the simulated magnetic resonance image in response to receiving the upsampled magnetic resonance image, wherein execution of the machine executable instructions further causes the computational system to receive the simulated magnetic resonance image in response to inputting the upsampled magnetic resonance image into the second resolution modality conversion neural network; and the memory further comprises a first resolution modality conversion neural network configured to convert the preliminary magnetic resonance image from the first magnetic resonance imaging modality to the second magnetic resonance imaging modality, wherein execution of the machine executable instructions further causes the computational system to receive a converted preliminary magnetic resonance image in response to inputting the preliminary magnetic resonance image into the first resolution modality conversion neural network, wherein the upsampling neural network is configured to output the upsampled magnetic resonance image as the simulated magnetic resonance image in response to receiving the converted preliminary magnetic resonance image as input.

5. The medical system of claim 1, wherein generating the motion corrected magnetic resonance image using the upsampled magnetic resonance image and the clinical k-space data comprises performing a motion-compensated reconstruction of the motion corrected magnetic resonance image using the upsampled magnetic resonance image or the simulated magnetic resonance image.

6. The medical system of claim 5, wherein the motion-compensated reconstruction is performed as an optimization that uses the upsampled magnetic resonance image or the simulated magnetic resonance image as a motion free image to be reconstructed.

7. The medical system of claim 6, wherein the motion-compensated reconstruction comprises determining a phase of the motion free image to be reconstructed using a phase map determined at least partially from the clinical k-space data.

8. The medical system of claim 6, wherein execution of the machine executable instructions further causes the computational system to:

calculating simulated k-space data by performing a Fourier transform of the simulated magnetic resonance imaging data or the upsampled magnetic resonance image; and detecting motion corrupted k-space data by comparing the simulated k-space data to the clinical k-space data; and limiting the optimization to the motion corrupted k-space data.

9. The medical system of claim 3, wherein the generating the motion corrected magnetic resonance image using the upsampled magnetic resonance image and the clinical k-space data comprises:

calculating simulated k-space data by performing a Fourier transform of the simulated magnetic resonance imaging data;

detecting motion corrupted k-space data by comparing the simulated k-space data to the clinical k-space data as it is acquired; and reacquiring the motion corrupted k-space data and/or adjusting the acquisition of the clinical k-space data to adjust for the subject motion.

10. The medical system of claim 3, wherein the generating the motion corrected magnetic resonance image using the upsampled magnetic resonance image and the clinical k-space data comprises:

calculating simulated k-space data by performing a Fourier transform of the simulated magnetic resonance imaging data;

determining motion parameters by comparing the simulated k-space data and the clinical k-space data; and reconstruct the motion corrected magnetic resonance image from the clinical k-space data using a motion-correction algorithm that receives the motion parameters as input.

11. The medical system of claim 1, wherein the preliminary k-space data is at least partially coil calibration k-space data acquired from multiple magnetic resonance imaging coil elements, wherein execution of the machine executable instructions further causes the computational system to:

reconstruct a coil image for each of the multiple magnetic resonance imaging coil elements from the coil calibration k-space data; and construct the preliminary magnetic resonance image by combining at least the coil image for each of the multiple magnetic resonance imaging coil elements.

12. The medical system of claim 1, wherein the preliminary k-space data is at least partially acquired from a body coil.

13. The medical system of claim 1, wherein the preliminary k-space data is magnetic resonance fingerprinting k-space data, wherein the preliminary magnetic resonance image is a quantitative magnetic resonance image.

14. A computer program comprising machine executable instructions stored on a non-transitory computer readable medium, which when executed by a computational system that is operatively coupled to an upsampling neural network, wherein the upsampling neural network is configured to output an upsampled magnetic resonance image with a second resolution in response to receiving a preliminary magnetic resonance image with a first resolution, wherein the second resolution is higher than the first resolution, wherein execution of the machine executable instructions causes the computational system to:

receive preliminary k-space data descriptive of a region of interest of a subject at the first resolution;

reconstruct the preliminary magnetic resonance image from the preliminary k-space data;

receive clinical k-space data descriptive of the region of interest of the subject at the second resolution;

input the preliminary magnetic resonance image into the upsampling neural network and receive from the upsampling neural network, the upsampled magnetic resonance image; and perform a motion-compensated reconstruction to generate a motion corrected magnetic resonance image using the upsampled magnetic resonance image and the clinical k-space data.

15. A method of medical imaging, wherein the method comprises:

receiving preliminary k-space data descriptive of a region of interest of a subject at the first resolution;

reconstructing a preliminary magnetic resonance image from the preliminary k-space data;

receiving clinical k-space data descriptive of the region of interest of the subject at a second resolution, wherein the second resolution is higher than the first resolution;

receiving an upsampled magnetic resonance image, from an upsampling neural network, in response to inputting the preliminary magnetic resonance image into the upsampling neural network, wherein the upsampling neural network is configured to output the upsampled magnetic resonance image with the second resolution in response to receiving the preliminary magnetic resonance image with the first resolution; and reconstruct the motion corrected magnetic resonance image using the upsampled magnetic resonance image and the clinical k-space data.

* * * * *